(12) United States Patent
Yamamoto et al.

(10) Patent No.: US 11,021,685 B2
(45) Date of Patent: Jun. 1, 2021

(54) OSTEOBLASTS AND METHOD FOR GENERATING SAME

(71) Applicant: KYOTO PREFECTURAL PUBLIC UNIVERSITY CORPORATION, Kyoto (JP)

(72) Inventors: Kenta Yamamoto, Kyoto (JP); Tsunao Kishida, Kyoto (JP); Toshiro Yamamoto, Kyoto (JP); Osam Mazda, Kyoto (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 185 days.

(21) Appl. No.: 15/900,930

(22) Filed: Feb. 21, 2018

(65) Prior Publication Data

US 2018/0195043 A1    Jul. 12, 2018

Related U.S. Application Data

(63) Continuation of application No. PCT/JP2016/074248, filed on Aug. 19, 2016.

(30) Foreign Application Priority Data

Aug. 21, 2015 (JP) ............................... JP2015-163880

(51) Int. Cl.

| | |
|---|---|
| *C12N 5/077* | (2010.01) |
| *C12N 5/074* | (2010.01) |
| *C12N 5/0735* | (2010.01) |
| *C12N 15/09* | (2006.01) |
| *C12N 5/10* | (2006.01) |

(52) U.S. Cl.
CPC ......... *C12N 5/0654* (2013.01); *C12N 5/0606* (2013.01); *C12N 5/0696* (2013.01); *C12N 5/10* (2013.01); *C12N 15/09* (2013.01)

(58) Field of Classification Search
None
See application file for complete search history.

(56) References Cited

U.S. PATENT DOCUMENTS

2010/0233804 A1* 9/2010 Zhou .................... C12N 5/0696
435/354

OTHER PUBLICATIONS

Zhao, Feng-Qi ("Zhao"; Front Biosci (Landmark Ed). 2013; 18: 1051-1071, Published online Jun. 1, 2013 (Year: 2013).*
Extended European Search Report dated Feb. 12, 2019 in corresponding European Patent Application No. 16839210.8.
Mizoshiri et al., "Transduction of Oct6 or Oct9 gene concomitant with Myc family gene induced osteoblast-like phenotypic conversion in normal human fibroblasts", Biochemical and Biophysical Research Communications, vol. 467, No. 4, 2015, pp. 1110-1116.
Yamamoto et al., "Direct conversion of human fibroblasts into functional osteoblasts by defined factors", Proceedings of the National Academy of Sciences of the United States of America, vol. 112, No. 19, 2015, pp. 6152-6157.
Tantin et al., "Oct transcription factors in development and stem cells: insights and mechanisms", Development, vol. 140, No. 14, 2013, pp. 2857-2886.

* cited by examiner

*Primary Examiner* — James D Schultz
(74) *Attorney, Agent, or Firm* — Wenderoth, Lind & Ponack, L.L.P.

(57) ABSTRACT

An object of the present invention is to provide a method for generating an osteoblast that is applicable to repair of a bone defect due to various tumors, injuries, surgeries, etc. and to treatment for bone resorption typified by a periodontal disease, bone fracture, osteoporosis, etc., and that has a low risk of carcinogenesis. Provided as a means for achieving this object is a method for generating an osteoblast from a somatic cell of a mammal, the method comprising introducing Oct9 gene or an expression product thereof into the somatic cell.

2 Claims, 10 Drawing Sheets

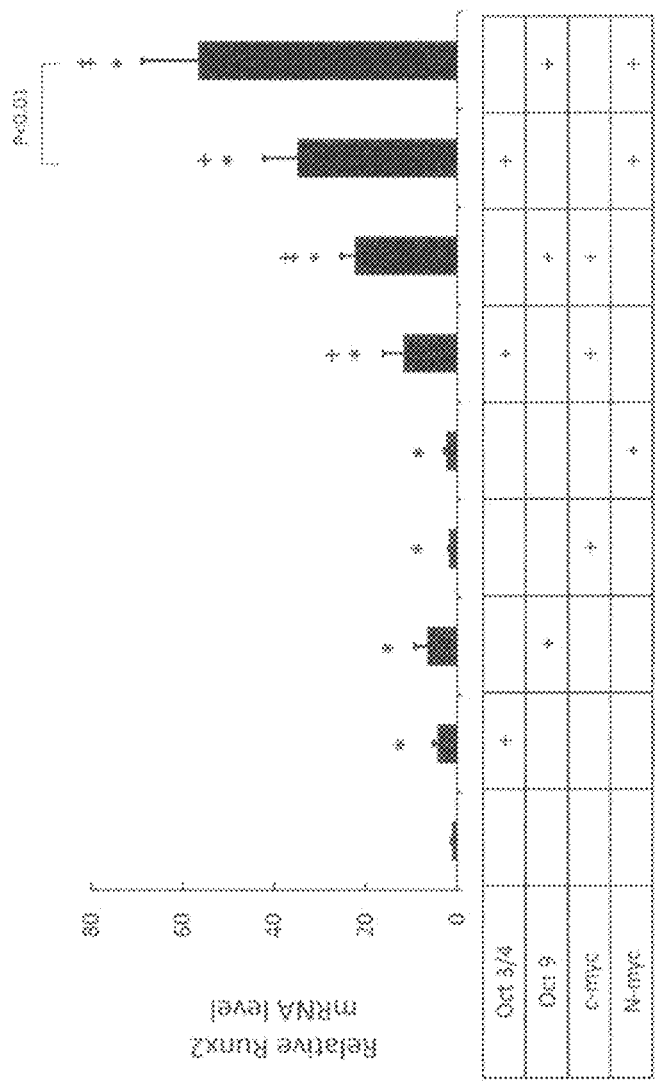

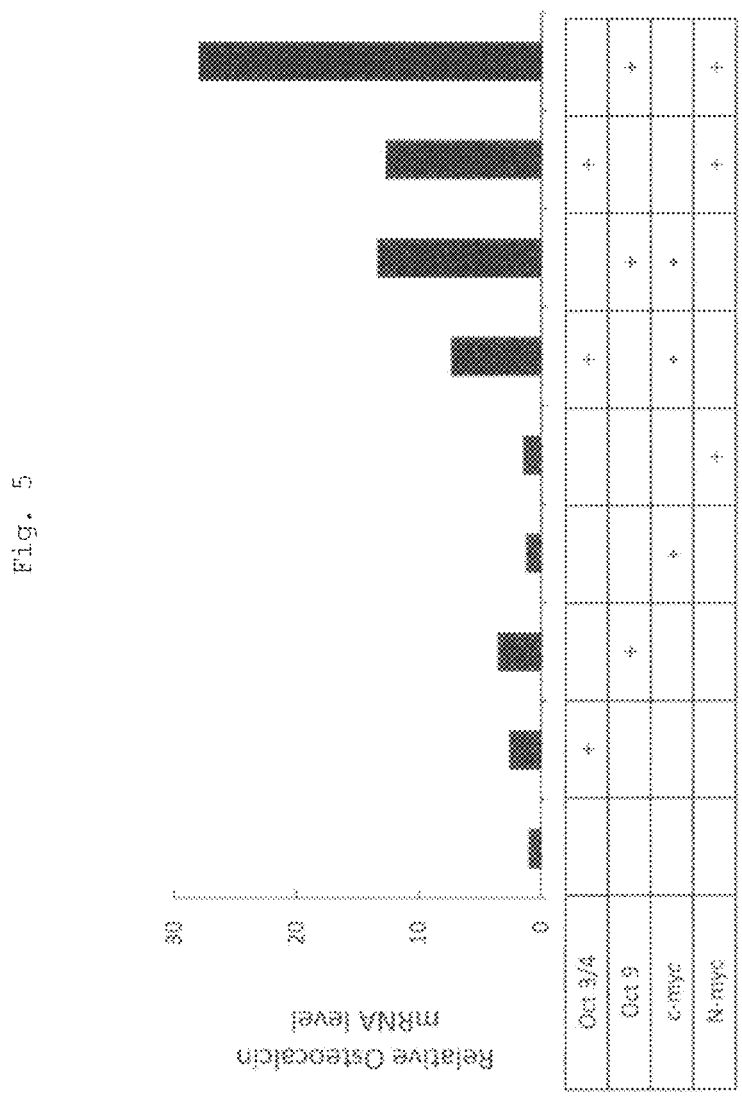

OSTEOBLASTS AND METHOD FOR GENERATING SAME

CROSS REFERENCES TO RELATED APPLICATIONS

This application is a continuation of International Patent Application No. PCT/JP2016/074248, filed on Aug. 19, 2016, and claims priority to Japanese Patent Application No. 2015-163880, filed on Aug. 21, 2015, all of which are incorporated herein by reference in their entireties.

BACKGROUND OF THE INVENTION

Field of the Invention

The present invention relates to an osteoblast and a method for generating the osteoblast; and more specifically, to a method for generating an osteoblast by direct reprogramming.

Discussion of the Background

Transplantation of osteoblasts to an affected area to repair a bone defect due to a bone tumor, injury, osteomyelitis, etc., or a bone defect after curettage of a bone tumor or the like, can be expected to promote bone formation and to improve functional and morphological prognosis. In fact, for example, treatment performed by autologous transplantation of bone marrow cells collected from the cancellous bone of a patient has been carried out, and the effectiveness of the treatment is known. In this case, osteoblasts obtained by differentiation induction from mesenchymal stem cells contained in autologous bone marrow cells are considered to contribute to bone formation and remodeling. On the other hand, the prevalence of osteoporosis has been increasing in step with the aging of the population, and bone fractures of elderly persons may lead to prolonged bed rest. Transplantation of osteoblasts is considered to be capable of promoting the healing of bone fracture due to osteoporosis, external injury, or the like; intractable bone fracture; and pseudofracture. In addition, the transplantation of the osteoblasts may also be useful for, for example, rheumatoid arthritis, idiopathic osteonecrosis of the femoral head, arthrosis deformans, lumbar spondylosis deformans, spinal canal stenosis, disc herniation, spondylolysis, spondylolytic spondylolisthesis, scoliosis, cervical spondylotic myelopathy, ossification of posterior longitudinal ligament, spinal cord injury, coxarthrosis, gonarthrosis, slipped capital femoral epiphysis, osteomalacia, bone repair after surgery (such as breastbone repair after cardiac surgery), repair of a defect associated with artificial ankle joint surgery, osteomyelitis, and osteonecrosis.

On the other hand, periodontal disease is also referred to as a fourth lifestyle-related disease, occurs at a very high prevalence in persons, and causes various systemic diseases. As periodontal disease progresses, bone resorption of the alveolar bone occurs. Therefore, if osteoblasts can be supplied to a local bone resorption site with high efficiency, it will lead to regenerative treatment of the alveolar bone.

When transplantation of osteoblasts is combined with bone transplantation, artificial bone transplantation, artificial joints, or implants, therapeutic effects may be enhanced.

As such osteoblasts for transplantation, bone marrow mesenchymal stem cells, bone marrow cells including bone marrow mesenchymal stem cells, and the like have been used. However, collection of the bone marrow is problematic. For example, the collection is highly invasive to a patient, and a sufficient number of bone marrow cells cannot be supplied in some cases. Alternatively, using human embryonic stem cells (ES cells) does not require the collection of bone marrow from a patient, and may supply a sufficient number of osteoblasts. However, in addition to ethical issues, it may cause a risk of tumorigenesis of residual ES cells after transplantation. Alternatively, using iPS cells does not require the collection of bone marrow from a patient, and may supply a sufficient number of osteoblasts. However, it may cause a risk of tumorigenesis of residual iPS cells after transplantation.

Non-patent Literature (NPL) 1 discloses introduction of a lentivirus vector including Osterix into human ES cells, and differentiation induction into osteoblasts in an osteogenic medium. Non-patent Literature (NPL) 2 and Non-patent Literature (NPL) 3 disclose obtaining of osteoblasts from mouse iPS cells through conversion into MSCs by differentiation induction in an osteogenic medium.

Non-patent Literature (NPL) 4 discloses obtaining of osteoblasts by introducing an adenovirus vector including Runx2 into mouse iPS cells, and subjecting the cells to differentiation induction in an osteogenic medium. As disclosed in Non-patent Literature (NPL) 1 to Non-patent Literature (NPL) 4, osteoblasts are generated from pluripotent stem cells, such as ES cells and iPS cells, by differentiation induction; therefore, the methods require long-tam culture, and incur the risk of carcinogenesis.

When a gene group of a tissue-specific transcription factor is introduced into somatic cells, direct differentiation induction into tissue cells can be achieved without conversion into iPS cells (direct reprogramming (direct conversion)). Regarding this, for example, the following has been reported:

mouse fibroblast→chondrocyte (SOX9+Klf4+c-Myc genes were introduced);
mouse fibroblast→cardiac muscle cell (GATA4+Mef2c+Tbx5 genes were introduced);
mouse fibroblast→liver cell (Hnf4α+(Foxa1, Foxa2, or Foxa3) genes were introduced);
mouse fibroblast→neural stem cell (for example, Sox2+FoxG1 genes were introduced); and
mouse or human cell→hematopoietic stem cell.

Patent Literature (PTL) 1 discloses a method for efficiently generating an osteoblast having a functionality by introducing a group of specific genes into somatic cells (direct conversion). However, better methods are still needed.

CITATION LIST

Patent Literature

PTL 1: WO2015/012377

Non-Patent Literature (NPL)

Non-patent Literature (NPL) 1: Karner E et al., J Cell Physiol, 2009.
Non-patent Literature (NPL) 2: Li F et al., J Cell Biochem, 2010.
Non-patent Literature (NPL) 3: Biloussova G et al., Stem cells, 2011.
Non-patent Literature (NPL) 4: Tashiro K et al. Stem cells, 2009.

SUMMARY OF THE INVENTION

Object of the Invention

An object of the present invention is to provide a method for generating an osteoblast that is applicable to repair of a bone defect due to various tumors, injuries, surgeries, etc., and to treatment for bone resorption typified by a periodontal disease, bone fracture, osteoporosis, etc.; and that incurs less risk of carcinogenesis.

The inventors of the present invention have found that osteoblasts can be obtained directly by introducing Oct9 gene or an expression product thereof into somatic cells of a mammal (direct reprogramming) without conversion into pluripotent stem cells, such as ES cells and iPS cells.

Item 1

A method for generating an osteoblast from a somatic cell of a mammal, comprising introducing Oct9 gene or an expression product thereof into the somatic cell.

Item 2

A method for generating an osteoblast from a somatic cell of a mammal, comprising introducing Oct9 gene or an expression product thereof, and at least one gene selected from the group consisting of c-Myc gene, L-Myc gene, and N-Myc gene or an expression product or products thereof, into the somatic cell.

Item 3

The method according to claim 1 or 2, wherein the somatic cell is a fibroblast.

Item 4

The method according to any one of items 1 to 3, further comprising culturing in an osteoblast induction medium the somatic cell into which the gene or genes or expression product or products thereof have been introduced.

Item 5

An osteoblast derived from a somatic cell of a mammal and having exogenous Oct9 gene or an expression product thereof.

The present invention includes an osteoblast and a generation method therefor.

Advantageous Effects of Invention

According to the present invention, osteoblasts can be provided from somatic cells by direct reprogramming in a short period of time. The osteoblasts can be induced easily from somatic cells of a person who undergoes transplantation. Accordingly, when osteoblasts themselves or bone tissues prepared from the cells are transplanted, problems, such as an immunological rejection response, do not occur. In addition, osteoblasts can be induced directly from somatic cells without conversion into iPS cells or ES cells, and hence problems due to pluripotent stem cells, such as carcinogenesis, can be avoided.

BRIEF DESCRIPTION OF DRAWINGS

FIG. 4 shows the results of measurement of Runx2 mRNA expression levels (relative mRNA amounts) by real-time RT-PCR. The introduced genes are indicated by "+".

FIG. 5 shows the results of measurement of osteocalcin mRNA expression levels (relative mRNA amounts) by real-time RT-PCR. The introduced genes are indicated by "+".

Figure 6:
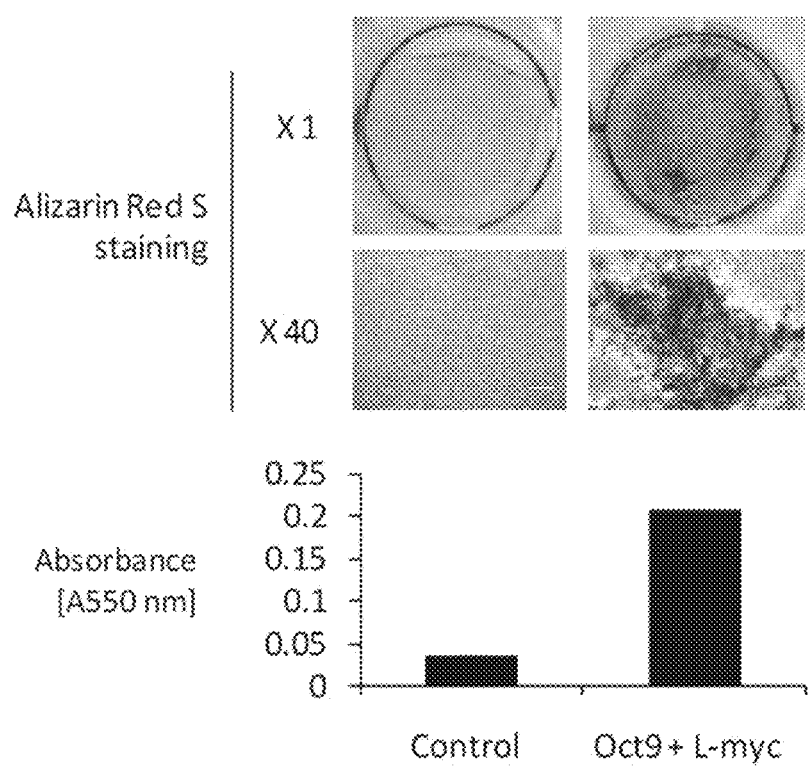

The upper section of FIG. 6 shows the results of Alizarin Red S staining by naked-eye images (magnification: ×1) and phase-contrast microscopic images (magnification: ×40). The lower section of FIG. 6 illustrates a graph of the staining intensity of Alizarin Red S staining.

Figure 7A:
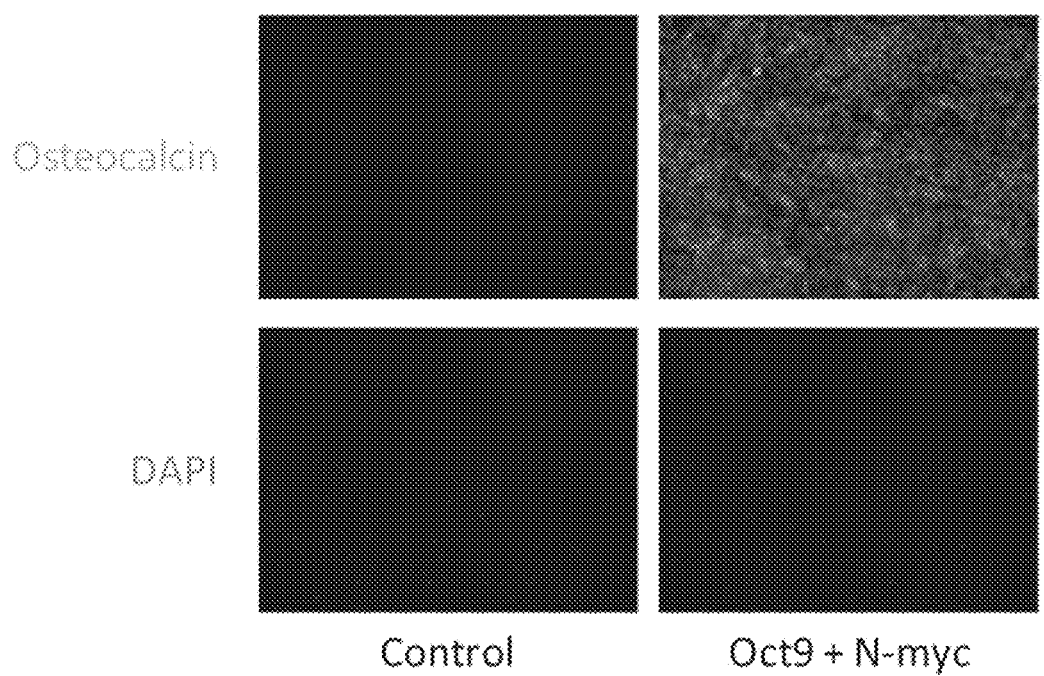

FIG. 7A shows immunostaining of osteocalcin. Nuclear DNA was co-stained with DAPI. The magnification was ×100.

Figure 7B:
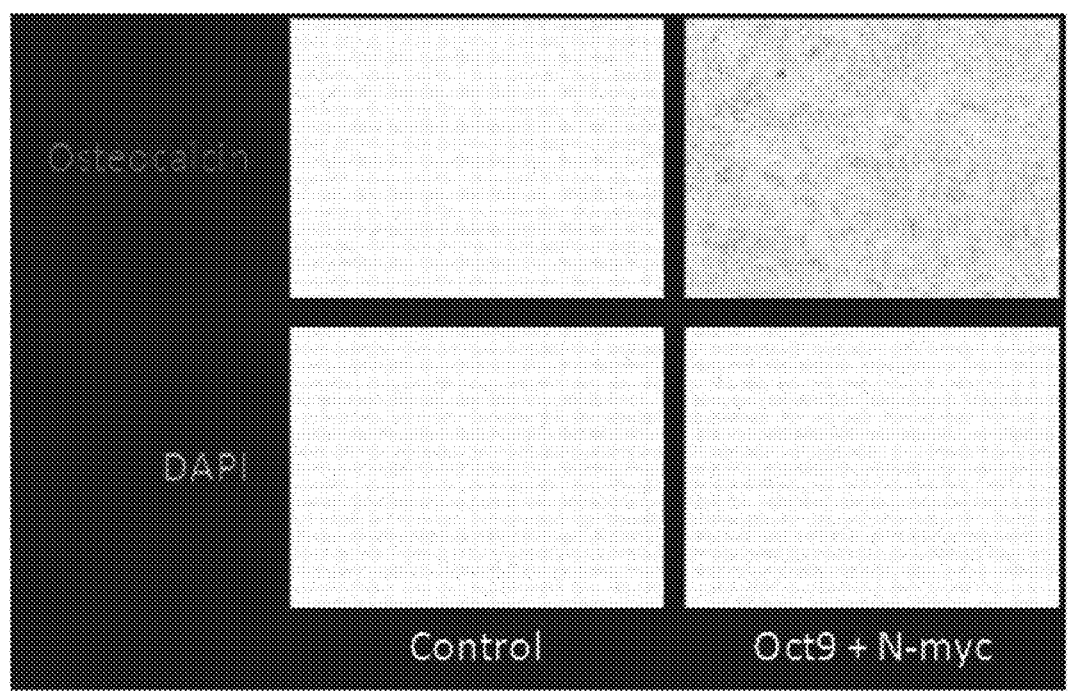

FIG. 7B shows a black-white inverted image of the immunostained osteocalcin image shown in FIG. 7A.

DETAILED DESCRIPTION OF THE PREFERRED EMBODIMENTS

The present invention provides a method for generating an osteoblast by converting a mammalian differentiated somatic cell into an osteoblast. The term "convert" herein means changing a somatic cell into a target osteoblast. One preferred embodiment of the method of the present invention provides a method of converting a somatic cell into an osteoblast without reprogramming of cells, such as production of iPS cells, which is also called "direct reprogramming" or "direct conversion."

In a preferred embodiment of the method of the present invention, a somatic cell is converted to an osteoblast without introducing a gene. The term "without introducing a gene" means that a somatic cell is converted to an osteoblast with no change of the original genomic sequence of the somatic cell (this mainly means the nucleotide sequence of DNA). Alternatively, the term "without introducing a gene" means that a somatic cell is converted to another somatic cell based on the function of the original endogenous gene.

Osteoblast

The present invention provides a method for generating an osteoblast. According to the present invention, preosteoblasts, immature osteoblasts, mature osteoblasts, bone cells, and the like can be generated. In this description, for the sake of convenience, all of the cells are referred to as "osteoblasts."

The existence of the osteoblast generated can be confirmed, for example, by detection of alkaline phosphatase (ALP) activity; detection of expression of marker genes, such as ALP, osteocalcin, osteopontin, and Runx2, by using, for example, real-time PCR for mRNAs; Alizarin Red S staining and von Kossa staining (production of mineralized bone matrix); or the like.

Runx2 is an essential transcription factor in bone formation. Runx2 plays an indispensable role in in vivo differentiation of mesenchymal stem cells into osteoblasts. Enforced expression of Runx2 in mesenchymal stem cells increases osteoblast-specific genes, such as OC (osteocalcin), BSP (bone sialo-protein), ALP (alkaline phosphatase), and COL1A1. In Runx2 knockout mice, intramembranous ossification or endochondral ossification never occurs due to the loss of mature osteoblasts; however, mesenchymal stem cells of this mouse are capable of being induced into adipocytes and chondrocytes.

ALP (alkaline phosphatase) is an early- to mid-stage osteoblast differentiation marker. ALP is contained in a large amount in the membrane surface of osteoblasts and in matrix vesicles secreted from osteoblasts, and is involved in the initiation of calcified matrix production.

Osteocalcin (OC) is specifically expressed in osteoblasts, and is believed to contribute to bone formation.

Alizarin Red S staining and von Kossa staining can detect the production, of mineralized bone matrix, i.e., calcium deposition, which is one of the important elements for bone formation.

Examples of diseases to be treated with osteoblasts (e.g., transplantation material) obtained by the present invention include bone defects due to bone tumors, injuries, osteomyelitis, and the like; bone defects after curettage of bone tumors or the like; bone fracture; osteoporosis; periodontal disease; alveolar bone resorption; rheumatoid arthritis; idiopathic osteonecrosis of the femoral head; arthrosis deformans; lumbar spondylosis deformans; spinal canal stenosis; disc herniation; spondylolysis; spondylolytic spondylolisthesis; scoliosis; cervical spondylotic myelopathy; ossification of posterior longitudinal ligament; spinal cord injury; coxarthrosis; gonarthrosis; capital femoral epiphysis; osteomalacia; reconstruction at a bone fracture site destroyed by complex fracture, such as lower jaw reconstruction; repair of bone after surgery (repair of breastbone after cardiac surgery); repair of a defect site associated with artificial ankle joint surgery; osteomyelitis; osteonecrosis; and the like. Further, when the osteoblasts are transplanted in combination with transplantation of bone, transplantation of artificial bone, and use of artificial joint, or implant, therapeutic effects may be enhanced. Additionally, when bone tissues prepared in vitro by culturing osteoblasts using a three-dimensional scaffold or the like so as to have various shapes are transplanted, the above-mentioned diseases can be treated. In addition to the diseases, various diseases involved in loss, lack, or decreased function of osteoblasts are targeted.

In this specification, unless otherwise specified, the term "treatment" refers to treatment for a patient suffering from a specific disease or disorder, and means to ameliorate the severity of the disease or disorder, ameliorate one or more symptoms thereof, or delay or reduce the speed of progress of the disease or disorder. In this specification, "treatment" includes "prevention."

The osteoblasts obtained in the present invention may be used not only for treatment of a disease, but also for beauty. For example, when the osteoblasts or bone tissue formed of the osteoblasts are transplanted to a defect site associated with an accident, surgery, or the like, the cells can produce a bone matrix to repair the defect site and to obscure the defect site by three-dimensional repair. In such a case, for expediency, treatment for humans is also referred to as treatment in this specification, the term "patient" can be replaced by the team "healthy subject" or "human," and the term "disease" can be replaced by the term "beauty."

The present invention can also be used not only for treatment for diseases of humans, but also for treatment for diseases of mammals including pets, such as dogs and cats; and livestock, such as cattle, horses, swine, sheep, and chickens. In such a case, the term "patient" is replaced by the term "livestock" or "mammal."

The transplantation material refers to an osteoblast-containing material to be introduced into a living body for repair and reconstruction of bone tissue. The transplantation material includes a material that partially or completely regenerates bone tissue in vitro, and is transplanted to the same or another individual. The osteoblasts obtained in the present invention can be used for preparation of the transplantation material. The osteoblasts themselves can also be used as the transplantation material. Accordingly, the osteoblasts can be transplanted to a patient as a cell preparation, can be transplanted together with a base (scaffold) formed of an artificial material, such as hydroxyapatite or bioabsorbable ceramic, or can be cultured with a scaffold, and then transplanted. In such case, the scaffold may form various three-dimensional shapes according to the purpose of transplantation.

Somatic Cell

The differentiated somatic cell of a mammal to be subjected to the method of the present invention is not particularly limited, as long as the cell is neither an osteoblast itself nor a cell that has no ability to differentiate into an osteoblast in vivo.

Any somatic cells derived from mammals can be used. When the osteoblasts are transplanted to a living body, somatic cells (autologous cells) derived from a test subject who undergoes transplantation are preferably used to reduce risks of infection, rejection responses, and the like. However, instead of the autologous cells, osteoblasts prepared in advance from somatic cells of other persons or other animals may be used for, for example, transplantation for sudden bone fracture or the like. Alternatively, osteoblasts can be prepared from somatic cells of another person or another animal prepared in advance, and used for transplantation. That is, an osteoblast bank or an osteoblast precursor cell bank can be prepared in advance, and used for transplantation. In such a case, in order to reduce risks, such as rejection responses, MHC typing can be carried out in advance. Further, characteristics and tumorigenicity of osteoblasts can be continued in advance.

In this specification, examples of mammals include mice, rats, hamsters, humans, dogs, cats, monkeys, rabbits, cows, horses, pigs, and the like. Humans are particularly preferable.

The present invention can also be used for, for example, various studies and development of technologies using osteoblasts. For example, the present invention is useful for basic studies such as analysis of osteogenesis, bone aging, morphogenesis, mechanisms of remodeling, mechanical stress against these factors, and influences of nutrients, immunity, nerves, and hormones. The present invention is also useful for, for example, analysis of the influence of internal exposure to a radioactive substance, such as strontium-90, on bone, and development of a technology for removing strontium-90 from bone.

The use of the present invention allows osteoblasts to be established from humans or animals having various diseases or genetic backgrounds in a simple, rapid, and inexpensive manner. Accordingly, abnormalities in osteoblasts related to the diseases or genetic backgrounds can be analyzed by, for example, a biochemical, molecular biological, or immunological technique. This can contribute to studies on clarification of pathogenic mechanisms of diseases and the like, or development of diagnostic methods. Development of drugs, toxicity tests of drugs, and the like using such osteoblasts can contribute to the development of novel treatment methods for various diseases.

The somatic cells as the subject of the method of the present invention (direct reprogramming) may be ex vivo or in vivo, and examples thereof include, but are not particularly limited to, fibroblasts, keratinocytes, oral mucosal epithelial cells, respiratory mucosal epithelial cells, gastric mucosal epithelial cells, intestinal mucosal epithelial cells, vascular endothelial cells, smooth muscle cells, adipocytes, gingival cells (gingival fibroblasts and gingival epithelial cells), dental pulp cells, periodontal ligament cells, leukocytes, lymphocytes, muscle cells, conjunctival epithelial cells, and osteoclasts, preferably fibroblasts, keratinocytes, oral mucosal epithelial cells, gingival cells, leukocytes, lymphocytes, and osteoclasts.

Examples of somatic cells also include somatic cells generated from somatic stem cells, such as mesenchymal stem cells (MSCs), neural stem cells, hepatic stem cells, intestinal stem cells, skin stem cells, hair follicle stem cells, and melanocyte stem cells, by induction of differentiation, dedifferentiation, or reprogramming. Examples of somatic cells also include somatic cells generated by inducing various somatic cells into other somatic cells by induction of differentiation, dedifferentiation, or reprogramming. Examples of somatic cells also include somatic cells generated from germ line cells by induction of differentiation, dedifferentiation, or reprogramming.

Examples of somatic cells also include somatic cells generated from embryonic stem cells (ES cells) or induced pluripotent stem cells (iPS cells) by induction of differentiation or reprogramming.

The "somatic cells" of the present invention also encompass ES cells, iPS cells, and germ line cells, although they are not, strictly speaking, somatic cells (in such a case, the term "somatic cells" should be read as "ES cells," "iPS cells," or "germ line cells").

Examples of somatic cells also include cultured cells and somatic cells generated from cultured cells by induction of differentiation, dedifferentiation, or reprogramming.

Gene

The method of the present invention contains a step of introducing Oct9 gene or an expression product thereof into somatic cells. The "gene" as used herein includes genomic DNA (usually double-stranded DNA) and cDNA (positive single-stranded DNA or double-stranded DNA) as long as they encode genetic information. The "expression product" includes mRNA or protein of the gene.

Oct9 (also referred to as POU class 3 homeobox 4, POU3F4, brain-specific homeobox/POU domain protein 4, brain-4, or Brn-4) is a transcription factor that belongs to class 3 of the POU domain family. Oct9 is considered to specifically bind to the octamer motif (ATGCAAAT). Oct9 is expressed in the brain (hypothalamus, hippocampus), inner ear, pancreas, etc. Oct9 is considered to be involved in differentiation of nerve cells, and is critically involved in differentiation of neural stem cells (Document A). Further, Oct9 is considered to play an important role in inner ear development, and deficiency of Oct9 is considered to cause hearing loss (Document B). However, the role of Oct9 osteoblasts is not known.

Document C shows that osteoblasts can be induced by introducing four factors of Runx2, Osterix, Oct3/4, and L-myc into fibroblasts, and that osteoblast-like cells can also be induced by introducing 2 factors of Oct4 and L-myc into fibroblasts. Document C thus concludes that Oct3/4 is a preferable gene. However, Oct3/4 has been reported to be expressed in a certain type of cancer (Documents D and E), and may be involved in tumorigenesis.

Document C is silent as to Oct9. In the present invention, however, the inventors found that introduction of Oct9 alone or co-introduction of Oct9 with a gene belonging to the myc family can convert fibroblasts into osteoblasts more efficiently than, or as efficiently as, Oct3/4. Unlike Oct3/4, Oct9 is not involved in carcinogenesis. Therefore, Oct9 may be more desirable than Oct3/4 in this respect.

Further, although N-myc gene is known to be involved in the development of neural origin and neuroendocrine tumors, involvement in bone tumors is not known (Document D). Therefore, osteoblasts induced by co-introducing Oct9 and N-Myc may have a low risk of tumorigenesis, and thus be desirable.

Document A: Tan X F, Qin J B, Jin G H, Tian M L, Li H M, Zhu H X, Zhang X H, Shi J H, Huang Z, (2010) Effects of Brn-4 on the neuronal differentiation of neural stem cells derived from rat midbrain. Cell Biol Int, 34: 877-882.

Document B: Braunstein E M, Crenshaw E B 3rd, Morrow B E, Adams J C, (2008) Cooperative function of Tbx1 and Brn4 in the periotic mesenchyme is necessary for cochlea formation. J Assoc Res Otolaryngol, 9: 33-43.

Document C: Direct conversion of human fibroblasts into functional osteoblasts by defined factors. Yamamoto K, Kishida T, Sato Y, Nishioka K, Ejima A, Fujiwara H, Kubo T, Yamamoto T, Kanamura N, Mazda O, Proc Natl Acad Sci USA, 2015 May 12; 112 (19): 6152-7

Document D: Jin T, Branch D R, Zhang X, Qi S, Youngson B, Goss P E, (1999) Examination of POU homeobox gene expression in human breast cancer cells. Int J Cancer, 81: 104-112

Document E: Wang P, Branch D R, Bali M, Schultz G A, Goss P E, Jin T, (2003) The POU homeodomain protein OCT3 as a potential transcriptional activator for fibroblast growth factor-4 (FGF-4) in human breast cancer cells. Biochem J, 375: 199-205

Document F: Beltran H, (2014) The N-myc Oncogene: Maximizing its Targets, Regulation, and Therapeutic Potential. 12: 815-822

In view of the high efficiency in converting somatic cells into osteoblasts, at least one member selected from the group consisting of c-Myc gene, L-Myc gene, and N-Myc gene or an expression product or products thereof may be introduced in addition to Oct9 gene. A combination of Oct9 gene and c-Myc gene, a combination of Oct9 gene and L-Myc gene, and a combination of Oct9 gene and N-Myc gene can be mentioned as part of embodiments of the present invention.

In the method of the present invention, unless the effect of the present invention is not impaired, one or more other genes may be introduced in addition to the gene or an expression product thereof. Examples of genes that can be introduced in addition thereto include Oct4 (also referred to as Oct3, Oct3/4) Oct1A, Oct6, Klf family (KLF1, KLF2, KLF3, KLF4, KLF5, KLF6, KLF7, KLF8, KLF9, KLF10, KLF11, KLF12, KLF13, KLF14, KLF15, KLF16, KLF17), Lin-28, Sox1, Sox2, Sox3, Sox7, Sox15, Sox17, Sox18, and like reprogramming genes. Bone-related genes, such as Runx2, Osterix, and Dlx5, can also be mentioned as examples. These genes can be used singly, or in a combination of two or more.

In the method of the present invention, the number of genes or expression products thereof, inclusive of Oct9 gene, may be one, or two or more. From the viewpoint of convenience, about 1 kind (only Oct9 gene or an expression product thereof) to about 4 kinds (Oct9 gene or an expression product thereof, and approximately three additional genes or expression products thereof), preferably 1 kind, 2 kinds (Oct9 gene or an expression product thereof, and one additional gene or an expression product thereof) or 3 kinds (Oct9 gene or an expression product thereof, and two additional genes or expression products thereof) can be used. As specific embodiments, Oct9 gene or an expression product thereof alone; and two species that are Oct9 gene or an expression product thereof, and at least one member selected from the group consisting of c-Myc gene, L-Myc gene, and N-Myc gene, or an expression product or products thereof can be mentioned.

All of the above genes are highly conserved in vertebrates. In this specification, the term "gene" refers to genes including homologues, unless a specific animal name is described. The genes further include genes having functions equivalent to those of wild-type gene products, even when the genes include mutations including polymorphisms.

For example, cDNA nucleotide sequences of human (Homo sapiens) Oct9 gene, c-Myc gene, L-Myc gene, and N-Myc gene, and amino acid sequences of proteins encoded by these sequences, have been registered at GenBank provided by the National Center for Biotechnology Information (NCBI), under the following accession numbers (it should be understood that when multiple revisions have been registered, each number refers to the latest revision):

human Oct9 gene mRNA sequence: NM_000307 (for example, NM_000307.4), human Oct9 protein amino acid sequence: NP_000298 (NP_000298.3); NM_002467.4→NP_002458.2 human c-Myc gene mRNA sequence: NM_002467 (for example, NM_002467.4), human c-Myc protein amino acid sequence: NP_002458 (for example, NP_002458.2);

human L-Myc gene mRNA sequence: NM_001033081, NM_001033082, NM_005376 (for example, NM_001033081.2, NM_001033082.2, NM_005376.4), human L-Myc protein amino acid sequence: NP_001028253, NP_001028254, NP_005367 (NP_001028253.1, NP_001028254.2, NP_005367.2);

human N-Myc gene mRNA sequence: NM_001293228, NM_001293231, NM_001293233, NM_005378 (for example, NM_001293228.1, NM_001293231.1, NM_001293233.1, NM_005378.5), human N-Myc protein amino acid sequence: NP_001280157, NP_001280160, NP_001280162, NP_005369 (for example, NP_001280157.1, NP_001280160.1, NP_001280162.1, NP_005369.2).

Introduction

The method of the present invention can be performed according to a known direct reprogramming method, except that specific genes are selected. For example, the method can be performed according to the method described in any one of the following documents:

Document 1: Direct reprogramming of fibroblasts into functional cardiomyocytes by defined factors. Masaki Ieda, Ji-Dong Fu, Paul Delgado-Olguin, Vasanth Vedantham, Yohei Hayashi, Benoit G. Bruneau, and Deepak Srivastava, Cell, 142: 375-386, 2010.

Document 2: Direct conversion of fibroblasts to functional neurons by defined factors. Thomas Vierbuchen, Austin Ostermeier, Zhiping P. Pang, Yuko Kokubu, Thomas C. Sudhof & Marius Wernig, Nature, 463: 1035-1041, 2010

Document 3: Induction of human neuronal cells by defined transcription factors. Pang Z P, Yang N, Vierbuchen T, Ostermeier A, Fuentes D R, Yang T Q, Citri A, Sebastiano V, Marro S, Sudhof T C, Wernig M, Nature, 476: 220-223, 2011.

Document 4: Generation of hyaline cartilaginous tissue from mouse adult dermal fibroblast culture by defined factors, Kunihiko Hiramatsu, Satoru Sasagawa, Hidetatsu Outani, Kanako Nakagawa, Hideki Yoshikawa, and Noriyuki Tsumaki, Journal of Clinical Investigation, 121: 640-657, 2011.

Document 5: Induction of functional hepatocyte-like cells from mouse fibroblasts by defined factors. Pengyu Huang, Zhiying He, Shuyi Ji, Huawang Sun, Dao Xiang, Changcheng Liu, Yiping Hu, XinWang & Lijian Hui, Nature, 475: 386-389, 2011.

Document 6: Direct conversion of mouse fibroblasts to hepatocyte-like cells by defined factors. Sayaka Sekiya & Atsushi Suzuki, Nature, 475: 390-393, 2011.

The contents of Documents 1 to 6 are incorporated herein by reference.

Alternatively, the method of the present invention can also be performed according to the method disclosed in Document C, which shows that osteoblasts can be induced by introducing 4 factors of Runx2, Osterix, Oct3/4, and L-myc into fibroblasts, or by introducing two factors of Oct3/4 and L-myc into fibroblasts (Document C).

Specifically, it is preferable that the gene to be introduced for conversion into osteoblasts (a combination of a bone-related gene and a reprogramming-related gene, or a reprogramming-related gene alone) is incorporated into an expression vector, and that the expression vector is introduced into target somatic cells to express the gene in the cells.

As a method of introducing a gene, there can also be used, for example, a method involving infection with a viral vector, such as a retrovirus vector, an adenovirus vector, a lentivirus vector, an adeno-associated virus vector, a herpesvirus vector, or a Sendai virus vector; and in the case of introduction of a gene and an expression product thereof, a method involving transfection with a plasmid vector, an episomal vector, or a gene expression product (mRNA, protein) by a non-viral vector, such as a cationic liposome, a cationic polymer, or electroporation. Alternatively, mRNA can also be introduced. In this description, all of the means to be used for gene introduction are collectively referred to as "vector."

By introducing a drug selective marker (conferring resistance to puromycin, blasticidin S, neomycin, hygromycin, etc.) with a therapeutic gene and then performing drug selection, cells that express a therapeutic gene can be selected and then used.

When factors to be introduced are an expression product of a bone-related gene and an expression product of a reprogramming-related gene (such as a protein), a peptide called "protein transduction domain (PTD)" may be bonded to a protein obtained as an expression product, and added to a medium to introduce the peptide into somatic cells. When some of the bone-related gene(s) are expressed in somatic cells used as a material of osteoblasts, it is not necessary to introduce the protein(s) encoded by the gene(s) from the outside. In addition, even when a reprogramming factor or a gene of a reprogramming factor is not introduced, osteoblasts can be induced with a small molecule used as an alternative. Examples thereof include methods described in "Generation of induced pluripotent stem cells using recombinant proteins." Zhou H, Wu S, Joo J Y, Zhu S, Han D W, Lin T, Trauger S, Bien G, Yao S, Zhu Y, Siuzdak G, Scholer H R, Duan L, Ding S, Cell Stem Cell, 2009 May 8; 4 (5): 381-4 and "Generation of human induced pluripotent stem cells by direct delivery of reprogramming proteins." Kim D, Kim C H, Moon J I, Chung Y G, Chang M Y, Han B S, Ko S, Yang E, Cha K Y, Lanza R, Kim K S, Cell Stem Cell, 2009 Jun. 5; 4 (6): 472-6.

The gene (e.g., genomic DNA, cDNA) introduced into somatic cells can be transcribed under the control of an appropriate promoter. For example, the gene can be transcribed by a long terminal repeat (LTR) promoter of a retroviral vector, or may be expressed from another promoter in a vector. For example, constitutive expression promoters, such as CMV promoter, EF-1α promoter, and CAG promoter, or desired inductive promoters may be used. Alternatively, a chimeric promoter obtained by replacing a portion of LTR with another promoter may also be used.

Culture

In the method of the present invention, differentiated somatic cells of mammals can be cultured in a medium after gene introduction (or transfer).

The culture can be performed in an appropriate container for containing the cells and medium. A preferred example of the technique of performing the culture is, but is not limited to, a technique of performing the culture at about 37° C. at a carbon dioxide concentration of about 5%. The culture under such conditions can be performed by using, for example, a known $CO_2$ incubator.

As long as the effect of the present invention is not impaired, the culture period is not particularly limited. For example, the culture period may be about 24 hours to about 60 days.

In culture, passage can be performed, if necessary. When passage is performed, the cells are collected before or immediately after the cells reach confluence, and the cells are seeded in fresh medium. In the culture of the present invention, the medium can be appropriately replaced.

Medium

The medium used in the method of the present invention is not particularly limited. Usual liquid media such as DMEM (Dulbecco's Modified Eagle's Medium) and EMEM (Eagle's Minimal Essential Medium) can be used. If necessary, serum components (Fetal Bovine Serum (FBS), Human Serum (HS)), antibacterial agents, such as streptomycin and penicillin, non-essential amino acids, and like components can be added.

In view of the high efficiency in osteoblast generation by the method of the present invention, the use of a differentiation-inducing medium for differentiation of osteoblasts as a medium is preferable. The "differentiation-inducing medium for inducing osteoblasts" refers to a medium containing components that allow pluripotent stem cells (such as embryonic stem (ES) cells or iPS cells) to differentiate into osteoblasts.

The differentiation-inducing medium for differentiation of osteoblasts is not particularly limited. For example, media containing ascorbic acid (L-ascorbic acid) or a salt thereof, β-glycerophosphoric acid (β-glycerophosphate) or a salt thereof, and adrenal cortical hormones, such as dexamethasone, can be used.

Specifically, the differentiation-inducing medium for differentiation of osteoblasts (bone-inducing medium) is, for example, a medium obtained by adding (for example, about 0.1 to 1000 μg/ml, preferably about 1 to 100 μg/ml) ascorbic acid; (for example, about 0.1 to 1000 mM, preferably about 1 to 100 mM) β-glycerophosphate; (about 1 nM to about 10 mM, preferably about 10 to 1000 mM) dexamethasone (all of the concentrations are final concentrations); and (at least one) component selected from the group consisting of glucocorticoids, such as hydrocortisone, to a normal liquid medium. One embodiment of the medium is, but is not limited to, a medium obtained by adding about 50 μg/ml ascorbic acid, about 10 mM β-glycerophosphate, and about 100 nM dexamethasone (all of the concentrations are final concentrations) to a normal medium, such as DMEM, containing 10% FBS and 5% HS. However, the medium is not limited thereto.

In this way, somatic cells are converted into osteoblasts, and osteoblasts are generated.

The existence of osteoblasts generated can be confirmed by the above-mentioned ALP staining, measurement of marker genes by real-time RT-PCR (reverse transcription polymerase chain reactor), RT-PCR, Alizarin Red S staining, von Kossa staining, or the like.

In one embodiment, the generated osteoblast contains exogenous Oct9 gene or an expression product thereof. The term "exogenous" as used herein means a gene or an expression product thereof that is different from native genes or expression products thereof and that is introduced mainly by the above introduction means. Examples of exogenous genes include genes whose expression is controlled by a promoter other than native promoters, genes present at non-native chromosomal loci, extrachromosomal genes, and the like.

EXAMPLES

Examples are described below. However, it should be understood that the present invention is not limited to these Examples.

Example 1

The full-length coding sequences of Oct1, Oct2, Oct5/7, Oct6, Oct8, Oct9, Oct11, and N-Myc were amplified by PCR, and were each inserted to the EcoRI site of retroviral vector plasmid pMXs (Cell Biolabs Inc., San Diego, Calif., USA; cat no. RTV-012). The retroviral vector plasmids constructed by inserting coding sequences of Oct3/4, c-Myc, and L-Myc to the EcoRI site of retroviral vector plasmids were kindly provided by Professor Yamanaka, Kyoto University, Japan. The PLAT-GP packaging cells (Cell Biolabs Inc., San Diego, Calif., USA; cat no. VPK-305) were seeded in 10-cm culture dishes at a concentration of $5.5 \times 10^6$/dish. On the following day, the cells were co-transfected with the plasmid vector of each gene and pCMV-VSV-G plasmid (Cell Biolabs Inc., San Diego, Calif., USA; cat no. RV-110) using an X-treme Gene 9 transfection reagent (Roche Applied Science, Penzberg, Germany). After 24 hours, the culture supernatant was removed by aspiration, and a fresh medium containing no antimicrobial agents was added. Then, after 24 hours, the culture supernatant was collected and filtrated through a filter with a pore size of 0.45 μm to obtain a virus suspension.

Normal human dermal fibroblasts (NHDF) were resuspended in a Dulbecco's minimum essential medium (DMEM) (complete medium) containing 10% fetal bovine serum (FBS), 0.1 mM non-essential amino acid, 100 μ/mL streptomycin, and 100 U/mL penicillin, and seeded in 35-mm dishes. The cells were cultured in 5% $CO_2$/95% humidified air at 37° C. On the following day, the culture supernatant was removed by aspiration. A medium containing a retroviral vector having the gene(s) shown in FIG. 1 and 4 μg/mL polybrene was added. After 24 hours, the supernatant was removed by aspiration, and a complete medium (osteogenic medium) containing 50 μg/mL ascorbic acid, 10 mM β-glycerol phosphate, and 100 nM dexamethasone was added. The medium was replaced with a fresh medium every 2-3 days.

Twenty-eight days after the gene introduction, total RNA was extracted. Using a probe and primers specific to Runx2 gene, a probe and primers specific to β-actin gene (Applied Biosystems), real-time RT-PCR was performed. The Runx2 gene mRNA level relative to the β-actin gene mRNA level was calculated. The relative Runx2 mRNA level was calculated with the value of the non-gene-introduced group being defined as 1.

Figure 1:
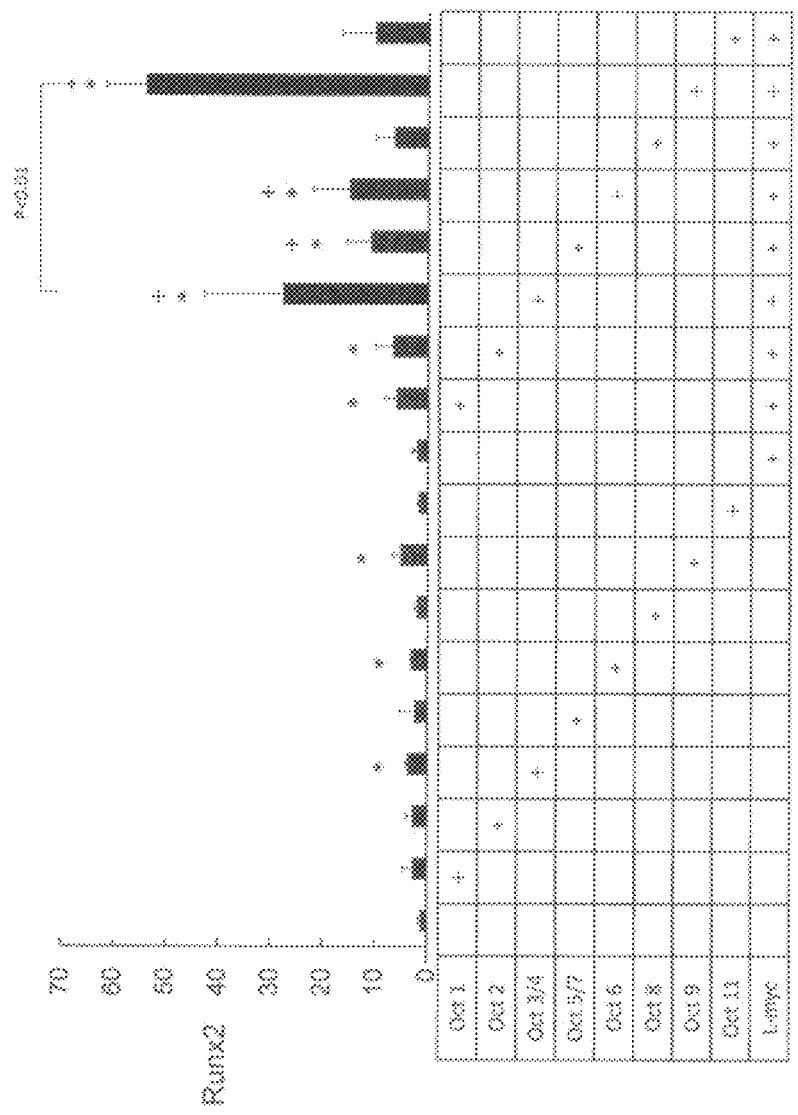
FIG. 1 shows the results of measurement of mRNA expression levels of Runx2 gene (relative mRNA amounts) by real-time RT-PCR. The introduced genes are indicated by "+".

FIG. 1 shows the results (average±standard deviation, n=3). In the groups to which Oct3/4, Oct6, Oct9, Oct1+L-myc, Oct2+L-myc, Oct3/4+L-myc, Oct5/7+L-myc, Oct6+L-myc, and Oct9+L-myc were introduced, the expression of mRNA of Runx2 was significantly induced. [*$p<0.05$ vs. non-gene-introduced control; +$p<0.05$ vs. L-myc alone]. In particular, the cells having Oct3/4 and L-myc or Oct9 and L-myc introduced thereinto highly expressed Runx2. Further, the cells having Oct9 and L-myc introduced thereinto most highly expressed Runx2.

Example 2

Normal human dermal fibroblasts (NHDF) were resuspended in a Dulbecco's minimum essential medium (DMEM) containing 10% fetal bovine serum (FBS), 0.1 mM non-essential amino acid, 100 μM/mL streptomycin, and 100 U/mL penicillin (complete medium), and seeded in 35-mm dishes. The fibroblasts were cultured at 37° C. in 5% $CO_2$/95% humidified air. On the following day, the culture supernatant was removed by aspiration. A medium containing a retroviral vector having the gene(s) shown in FIG. 1 and 4 μg/mL polybrene was added. After 24 hours, the supernatant was removed by aspiration, and a complete medium (osteogenic medium) containing 50 μg/mL ascorbic acid, 10 MM β-glycerol phosphate, and 100 nM dexamethasone was added. The medium was replaced with a fresh medium every 2-3 days.

Twenty-eight days after the gene introduction, the cells were fixed with 4% paraformaldehyde. After that, an anti-Runx2 antibody (Abnova, Taipei, Taiwan) was added, and the cells were incubated. A second antibody conjugated to Alexa Fluor 488 was then added, and nuclei were stained with DAPI. As a control, fibroblasts were also stained in the same way. The cells were observed under a fluorescent microscope at 100× magnification.

Figure 2A:
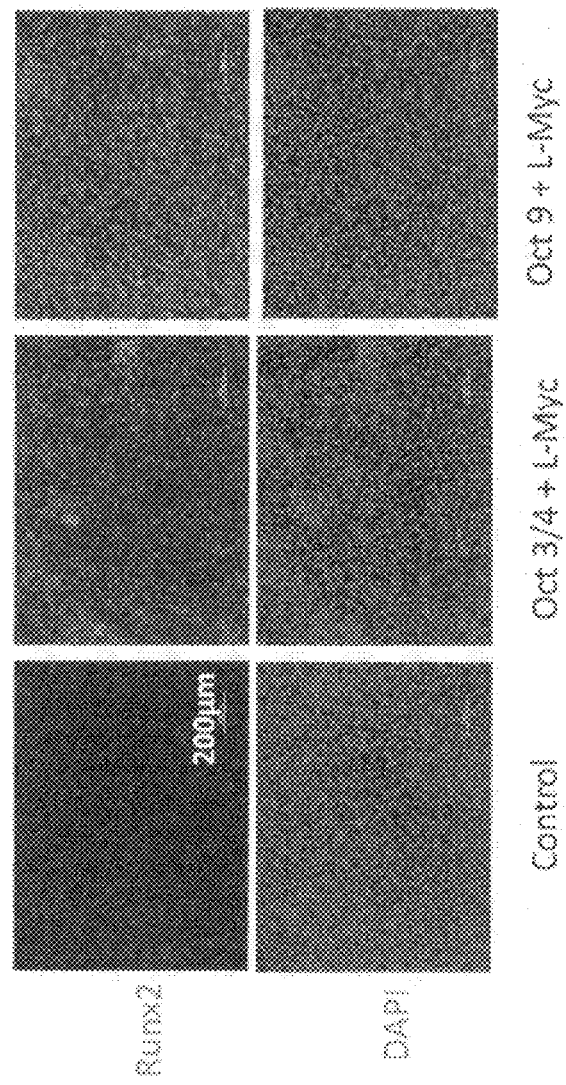
FIG. 2A shows immunostaining of Runx2. Nuclear DNA was co-stained with DAPI. The magnification was ×100. Scale bar=200 µm.
Figure 2B:
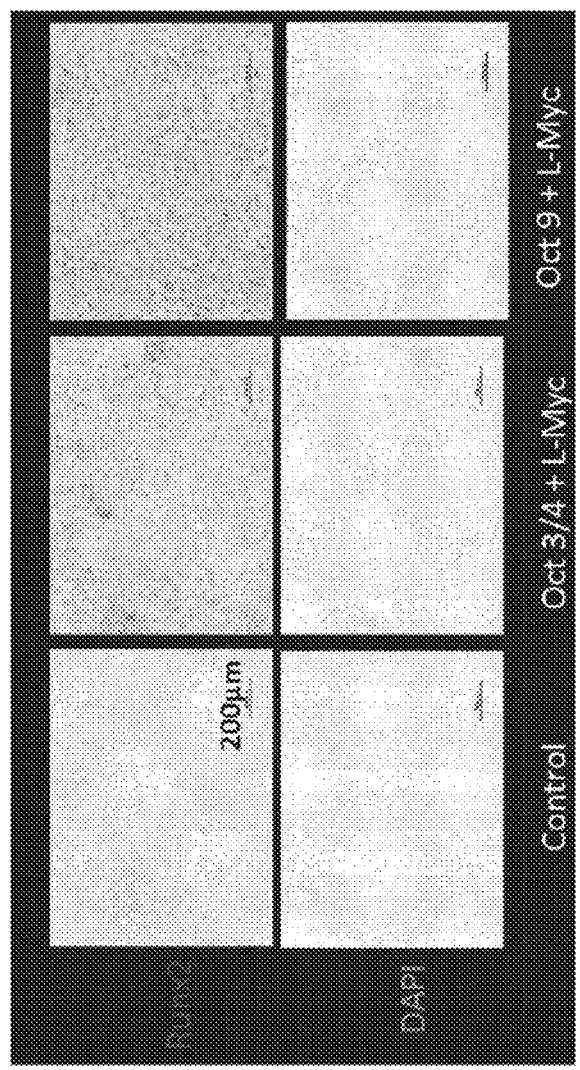
FIG. 2B shows monochrome inversion reverse-view images of the immunostained Runx2 shown in FIG. 2A.

FIG. 2 shows the results (Scale bar=200 μm. The results show that the fibroblasts did not express Runx2 protein at all, whereas the cells into which Oct3/4 and L-myc or Oct9 and L-myc were introduced exhibited the Runx2 protein. The results show that in particular, the cells into which Oct9 and L-myc were introduced more highly expressed Runx2 than the cells in which Oct3/4 and L-myc were introduced.

Example 3

Normal human dermal fibroblasts (NHDF) were resuspended in a Dulbecco's minimum essential medium (DMEM) (complete medium) containing 10% fetal bovine serum (FBS), 0.1 mM non-essential amino acid, 100 μg/mL streptomycin, and 100 U/mL penicillin, and seeded in 35-mm dishes. The cells were cultured in 5% $CO_2$/95% humidified air at 37° C. On the following day, the culture supernatant was removed by aspiration. A medium containing a retroviral vector having the gene(s) shown in FIG. 1 and 4 μg/mL polybrene was added. After 24 hours, the supernatant was removed by aspiration, and a complete medium (osteogenic medium) containing 50 μg/mL ascorbic acid, 10 MM β-glycerol phosphate, and 100 nM dexamethasone was added. The medium was replaced with a fresh medium every 2-3 days.

Twenty-eight days after the gene introduction, the cells were fixed with 4% paraformaldehyde. After that, an anti-Runx2 antibody (Abnova, Taipei, Taiwan) was added, and the cells were incubated. A second antibody conjugated to Alexa Fluor 488 was then added, and nuclei were stained with DAPI. As a control, fibroblasts were also stained in the same way. The cells were observed under a fluorescent microscope at 100× magnification.

Figure 3A:
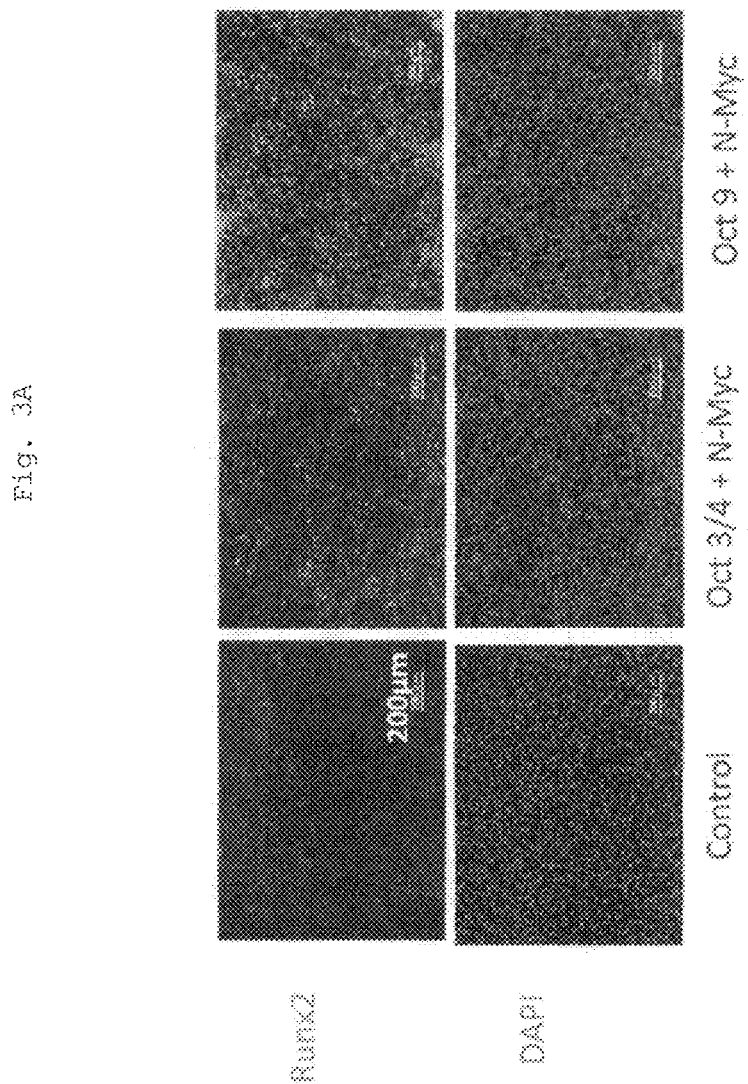
FIG. 3A shows immunostaining of Runx2. Nuclear DNA was co-stained with DAPI. The magnification was ×100. Scale bar=200 µm.
Figure 3B:
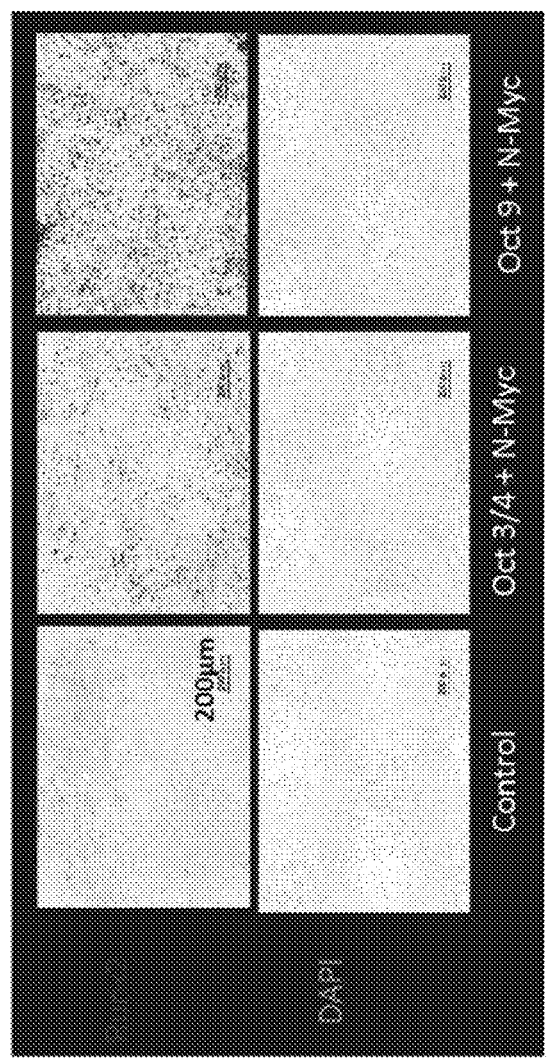
FIG. 3B shows a black-white inverted image of the immunostained Runx2 image shown in FIG. 3A.

FIG. 3 shows the results (Scale bar=200 μm). The results show that the fibroblasts did not express Runx2 protein at all, whereas the cells into which Oct3/4 and L-myc or Oct9 and L-myc were introduced exhibited the protein. The results show that in particular, the cells into which Oct9 and L-myc were introduced more highly expressed Runx2 than the cells into which Oct3/4 and L-myc were introduced.

Example 4

Normal human dermal fibroblasts (NHDF) were resuspended in a Dulbecco's minimum essential medium (DMEM) (complete medium) containing 10% fetal bovine serum (FBS), 0.1 mM non-essential amino acid, 100 μg/mL streptomycin, and 100 U/mL penicillin, and seeded in 35-mm dishes. The cells were cultured in 5% $CO_2$/95% humidified air at 37° C. On the following day, the culture supernatant was removed by aspiration. A medium containing a retroviral vector having the gene(s) shown in FIG. 1 and 4 μg/mL polybrene was added. After 24 hours, the supernatant was removed by aspiration, and a complete medium (osteogenic medium) containing 50 μg/mL ascorbic acid, 10 mM β-glycerol phosphate, and 100 nM dexamethasone was added. The medium was replaced with a fresh medium every 2-3 days.

Twenty-eight days after the gene introduction, total RNA was extracted from the cells. Using a probe and primers specific to Runx2 gene, and a probe and primers specific to β-actin gene (Applied Biosystems), real-time RT-PCR was performed. The Runx2 gene mRNA level relative to the β-actin gene mRNA was calculated. The relative Runx2 mRNA level was calculated with the value of the non-gene-introduced group being defined as 1.

FIG. 4 shows the results (average±standard deviation, n=3). [*$p<0.05$ vs. non-gene-introduced control; +$p<0.05$ vs. Oct3/4 alone; ‡$p<0.05$ vs. Oct9 alone.]

The results show that the cells into which Oct3/4, Oct9, c-myc, N-myc, Oct3/4+c-myc, Oct9+c-myc, Oct3/4+N-myc, or Oct9+N-myc had been introduced expressed the Runx2 gene mRNA significantly highly. In particular, the cells into which Oct9 and N-myc had been introduced expressed Runx2 most highly.

Example 5

Normal human dermal fibroblasts (NHDF) were resuspended in a Dulbecco's minimum essential medium (DMEM) containing 10% fetal bovine serum (FBS), 0.1 mM non-essential amino acid, 100 μg/mL streptomycin, and 100 U/mL penicillin (complete medium), and seeded in 35-mm dishes. The cells were cultured in 5% $CO_2$/95% humidified air at 37° C. On the following day, the culture supernatant was removed by aspiration. A medium containing a retroviral vector having the gene(s) shown in FIG. 1 and 4 μg/mL polybrene was added. After 24 hours, the supernatant was removed by aspiration, and a complete medium (osteogenic medium) containing 50 μg/mL ascorbic acid, 10 MM β-glycerol phosphate, and 100 nM dexamethasone was added. The medium was replaced with a fresh medium every 2-3 days.

Twenty-eight days after the gene introduction, total RNA was extracted from the cells. Using a probe and primers specific to osteocalcin gene, and a probe and primers specific to β-actin gene (Applied Biosystems), real-time RT-PCR was performed. The gene mRNA level relative to the β-actin gene mRNA was calculated. The relative osteocalcin mRNA level was calculated with the value of the non-gene-introduced group being defined as 1.

FIG. 5 shows the results. [*$p<0.05$ vs. non-gene-introduced control; +$p<0.05$ vs. Oct3/4 alone; ‡$p<0.05$ vs. Oct9 alone.]

The results show that the cells into which Oct3/4, Oct9, c-myc, N-myc, Oct3/4+c-myc, Oct9+c-myc, Oct3/4+N-myc, and Oct9+N-myc had been introduced expressed the osteocalcin gene mRNA significantly highly. In particular, the cells into which Oct9 and N-myc had been introduced expressed Runx2 most highly.

Example 6

Normal human dermal fibroblasts (NHDF) were resuspended in a Dulbecco's minimum essential medium (DMEM) (complete medium) containing 10% fetal bovine serum (FBS), 0.1 mM non-essential amino acid, 100 μg/mL streptomycin, and 100 U/mL penicillin, and seeded in 35-mm dishes. The cells were cultured in 5% $CO_2$/95% humidified air at 37° C. On the following day, the culture supernatant was removed by aspiration. A medium containing a retroviral vector having Oct9 and N-myc genes and 4 μg/mL polybrene was added. After 24 hours, the supernatant was removed by aspiration, and a complete medium (osteogenic medium) containing 50 μg/mL ascorbic acid, 10 MM β-glycerol phosphate, and 100 nM dexamethasone was added. The medium was replaced with a fresh medium every 2-3 days.

Twenty-eight days after the gene introduction, the culture medium was removed by aspiration from the culture dishes, and the cells were washed twice with PBS and fixed with 95% ethanol. After the cells were washed with sterile distilled water, an Alizarin Red S staining solution was added thereto, and the resulting mixture was allowed to stand at room temperature for 15 minutes. As a control, fibroblasts were also stained in the same way.

The upper section of FIG. 6 photographically shows the results by providing naked-eye images of the dishes (magnification: ×1) and phase-contrast microscopic images of the dishes (magnification: ×40) (scale bar=500 μm). The stained portion is calcified bone matrix (the calcified bone matrix stained red actually).

Further, after the Alizarin Red S staining solution was removed from all of the wells and the cells were washed with sterile distilled water, 10% Triton X was added thereto and the resulting mixture was allowed to react at room temperature for 1 hour. The fluid was collected from each well and transferred to a 96-well plate. The graph in the lower section of FIG. 6 shows the results of measuring the absorbance (550 nm) of the reaction solutions using a microplate reader. The absorbance is plotted on the vertical axis of the graph. The graph shows that as the absorbance is higher, a larger amount of calcified bone matrix is produced.

These results show that the cells into which Oct9 gene and L-myc gene had been co-introduced produced a large amount of calcified bone matrix and that the cells were highly efficiently converted into functional osteoblasts.

Example 7

Normal human dermal fibroblasts (NHDF) were resuspended in a Dulbecco's minimum essential medium (DMEM) (complete medium) containing 10% fetal bovine serum (FBS), 0.1 mM non-essential amino acid, 100 μg/mL streptomycin, and 100 U/mL penicillin, and seeded in 35-mm dishes. The cells were cultured in 5% $CO_2$/95% humidified air at 37° C. On the following day, the culture supernatant was removed by aspiration. A medium containing a retroviral vector having Oct9 and N-myc genes and 4 μg/mL polybrene was added. After 24 hours, the supernatant was removed by aspiration, and a complete medium (osteogenic medium) containing 50 μg/mL ascorbic acid, 10 mM β-glycerol phosphate, and 100 nM dexamethasone was added. The medium was replaced with a fresh medium every 2-3 days.

Twenty-eight days after the gene introduction, the cells were fixed with 4% paraformaldehyde. An anti-osteocalcin antibody (AbD Serotec, Kidlington, UK) was then added, and the cells were incubated. After that, the second antibody conjugated to Alexa Fluor 488 was added, and nuclei were stained with DAPI. As a control, fibroblasts were stained in the same way. The cells were observed under a fluorescent microscope at 100× magnification.

FIG. 7 shows the results. The results show that fibroblasts did not express osteocalcin protein at all, whereas the cells into which Oct9 and N-myc were introduced highly expressed osteocalcin.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for generating an osteoblast from a somatic cell of a mammal, comprising a step of introducing Oct9 gene or an expression product thereof into the somatic cell and further comprising culturing in an osteoblast induction medium the somatic cell into which the gene or genes or expression product or products thereof have been introduced, wherein the somatic cell is a fibroblast.

2. The method according to claim 1, comprising introducing Oct9 gene or an expression product thereof and at least one gene selected from the group consisting of c-Myc gene, L-Myc gene, and N-Myc gene or an expression product or products thereof into the somatic cell.

* * * * *